(12) United States Patent
Chang et al.

(10) Patent No.: US 12,239,695 B2
(45) Date of Patent: Mar. 4, 2025

(54) COMPOSITION COMPRISING THROMBIN-TREATED STEM CELL-DERIVED EXOSOME FOR TREATING SKIN WOUND

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); So Yoon Ahn, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 685 days.

(21) Appl. No.: 16/314,725

(22) PCT Filed: Jun. 27, 2017

(86) PCT No.: PCT/KR2017/006776
§ 371 (c)(1),
(2) Date: Jan. 2, 2019

(87) PCT Pub. No.: WO2018/004237
PCT Pub. Date: Jan. 4, 2018

(65) Prior Publication Data
US 2019/0314469 A1    Oct. 17, 2019

(30) Foreign Application Priority Data

Jul. 1, 2016  (KR) .................. 10-2016-0083703
Jun. 26, 2017 (KR) .................. 10-2017-0080366

(51) Int. Cl.
| | |
|---|---|
| *A61K 38/48* | (2006.01) |
| *A61K 9/12* | (2006.01) |
| *A61K 9/70* | (2006.01) |
| *A61K 35/28* | (2015.01) |
| *A61P 17/02* | (2006.01) |

(52) U.S. Cl.
CPC ............ *A61K 38/4833* (2013.01); *A61K 9/12* (2013.01); *A61K 9/70* (2013.01); *A61K 35/28* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 2015/0024011 A1* | 1/2015 | Lim | A61Q 7/00 424/400 |
| 2015/0125950 A1 | 5/2015 | Lim et al. | |
| 2016/0333317 A1* | 11/2016 | Chang | C12N 5/0665 |

FOREIGN PATENT DOCUMENTS

| | | | | |
|---|---|---|---|---|
| KR | 10-2014-0066456 A | 6/2014 | | |
| WO | WO-2015-052527 A1 | 4/2015 | | |
| WO | WO-2015088288 A1 * | 6/2015 | .......... | A61K 9/0019 |
| WO | WO-2015-142061 A1 | 9/2015 | | |

OTHER PUBLICATIONS

Zhang, Bin et al. HucMSC-Exosome Mediated-Wnt4 Signaling Is Required for Cutaneous Wound Healing. Stem Cells (2015)(33). pp. 2158-2168. (Year: 2015).*
Zhang (HucMSC-Exosome Mediated-Wnt4 Signaling Is Required for Cutaneous Wound Healing, 2014) (Year: 2014).*
Neufeld, Gera et al. Vascular endothelial growth factor (VEGF) and its receptors. The FASEB Journal. vol. Jan. 13, 1999. (Year: 1999).*
Wu Y, Chen L, Scott PG, et al. Mesenchymal stem cells enhance wound healing through differentiation and angiogenesis. Stem Cells 2007;26:2648-2669. (Year: 2007).*
Extended European Search Report in European Patent Application No. 17820513.4, dated Feb. 24, 2020.
Office Action from corresponding Japanese Patent Application No. 2018-568285, dated Apr. 7, 2020.
Iizuka, H., et al.; "Regulation of Keratinocyte Proliferation during Wound Healing", vol. 38, No. 1, pp. 132-147, 1996.
Inoue, H., et al.; Inflammation and Regeneration, vol. 24, No. 6, Nov. 2004, pp. 656-660.
Author Unknown, "Regeneration of Skin", vol. 60, No. 6, pp. 441-447, 2002.
Luo, G., et al. (2010) "Promotion of Cutaneous Wmmd Healing by Local Application of Mesenchymal Stem Dells Derived from Human Umbilical Cord Blood.", *Wound Repair and Regeneration*, vol. 18, p. 506--513. (Abstract Only).
Zhang, R., et al. (2015) "HucMSC-exosome Mediated-Wnt4 Signaling is Required for Cutaneous Wound Healing.", *Stem Cells*, vol. 33, pp. 2158-2168.
Zhang, B., et al. (2015) "Human Umbilical Cord Mesenchymal Stem Ceil Exosomes Enhance Angiogenesis Through the Wnt4/B-Catenin Pathway.", *Stem Cells Translational Medicine*, vol. 4, pp. 513-522.

(Continued)

*Primary Examiner* — Nghi V Nguyen
(74) *Attorney, Agent, or Firm* — Harness, Dickey & Pierce, P.L.C.

(57) ABSTRACT

The present disclosure relates to a pharmaceutical composition comprising an exosome derived from a thrombin-treated stem cell as an effective ingredient for preventing or treating a skin wound, a pharmaceutical formulation containing the same, and a production method thereof. Being a cell-free agent, an exosome-based therapeutic agent of the present disclosure has a low risk of carcinogenesis and no problems of graft rejection as well as being little liable to occur microvascular obstruction. The agent, which is not a cell, but a material isolated from a cell, can be subjected to medication development into an off-the-shelf product which allows for the reduction of production cost. The agent has the advantage of exhibiting outstanding angiogenesis and skin wound treatment effects even at a low concentration of exosomes thanks to the thrombin treatment effect.

7 Claims, 9 Drawing Sheets

(56) References Cited

OTHER PUBLICATIONS

International Search Report (ISR) from corresponding PCT Application No. PCT/KR2017/006776, dated Sep. 20, 2017, and its English translation.
Office Action dated Jan. 19, 2018 issued in Korean Patent Application No. KR10-2017-0080366.
Office Action from corresponding Chinese Patent Application No. 201780047575.0, dated Dec. 3, 2021.
Wang, L., et al.; "Advances of induced pluripotent stem cells in the regeneration of sweat gland", Chin J Injury Repair and Wound Healing, Dec. 2015, vol. 10 No. 6., p. 535-538.

* cited by examiner

COMPOSITION COMPRISING THROMBIN-TREATED STEM CELL-DERIVED EXOSOME FOR TREATING SKIN WOUND

CROSS-REFERENCE TO RELATED APPLICATIONS

This application is a national phase application of PCT Application No. PCT/KR2017/006776, filed 27 Jun. 2017, which claims benefit of Korean Patent Application Nos. 10-2016-0083703, filed on 1 Jul. 2016 and 10-2017-0080366, filed on 26 Jun. 2017. The entire disclosures of the applications identified in this paragraph are incorporated herein by references.

FIELD

The present disclosure relates to a pharmaceutical composition for preventing or treating a skin wound, which includes an exosome derived from thrombin-treated stem cells as an active ingredient, a pharmaceutical formulation containing the same, and a method of preparing the same.

BACKGROUND

Skin as a protective barrier for protecting the body is the body's primary line against a disease, and the epidermis provides a barrier against microbial invasion. Accordingly, the primary goal in the treatment of wounds, burns, abrasions and other injuries to the skin is rapid closure and wound healing to prevent infection.

Here, the wound healing is a complicated process generally including three steps of inflammation, proliferation and remodeling. The first step involves clotting for attaining hemostasis, supplementation of neutrophils to destroy bacteria and necrotic tissue, and supplementation of macrophages. In the second step, angiogenesis occurs, at this time, endothelial cells move to a wound site, and at the same time, fibroblasts move to the wound site to help in producing granulation tissue. The formation of granulation tissue results in reepithelialization. In the final step, collagen production and breakdown levels are equal, and the healed wound is slowly modulated in order to achieve the maximum strength. When even one of the above procedures does not properly function in a timely manner, the wound healing may be delayed or injured, resulting in a chronic state.

A chronic wound is defined as an open wound in which the skin requiring treatment for eight weeks or more is open, and an impaired healing process can often be associated with diabetic complications, resulting in severe amputations and even death. Approximately, 15% of diabetic patients suffer from chronic wounds that cannot be cured. Therefore, wounds are important issues for individuals as well as societies, and rapid treatment at the early stage may reduce the risk of secondary infection.

Effective wound healing requires highly organized, integrated coordination through complicated molecular biological events including extra-cellular matrix (ECM) deposition, cell proliferation/migration. One of the major factors relevant to the generation of chronic wounds is an injury to the cytokine secretory system secreted by local fibroblasts and inflammatory cells, resulting in a decrease in angiogenesis.

Meanwhile, stem cells are known as cells involved in the regeneration, treatment and immune responses of tissues as well as multipotency, and there have been efforts to isolate and culture mesenchymal stem cells from umbilical cord blood, bone marrow, etc. using these characteristics to develop a therapeutic agent for various diseases and symptoms.

However, such a treatment method using stem cells has the following side effects:

First, basically, a cell therapeutic agent cannot exclude the possibility of tumorogenicity due to DNA transfer; second, vascular obstruction or myocardial infarction may be caused due to stem cells having a large size; third, there is rejection due to a cell surface antigen in transplantation (allograft) using allogeneic cells such as cord blood; and fourth, in general, a cell therapeutic agent has a difficult manufacturing process and many restrictions on storage and transportation.

As such, due to the inherent limitations of stem cells, for reducing side effects and improving a therapeutic effect, a method for improving efficacy using genetic manipulation has been developed, but there are no clear alternatives to date.

Exosomes are small vesicles (approximately 30 to 100 nm in diameter) having a membrane structure secreted from various cells, and electron microscopic studies showed that the exosomes originated from specific compartments in cells called multivesicular bodies (MVBs), not directly detached from the plasma membrane, and released or secreted from the cells. That is, when fusion of the plasma membrane with MVBs occurs, small vesicles are released to an extracellular environment, and called exosomes. While it has not been clearly revealed what molecular mechanism is used to form such exosomes, it has been known that various types of immune cells including B-lymphocytes, T-lymphocytes, dendritic cells, platelets, macrophages, etc. as well as red blood cells, tumor cells and stem cells are also secreted by producing exosomes in a living state.

Particularly, it has been known that exosomes derived from stem cells contain nuclear components as well as receptors and proteins, and play a role in intracellular communication. In addition, the exosomes derived from stem cells contain relatively less animal serum, compared with stem cells, and thus the risk of a symptom caused by animal serum infection (zoonosis) may also be excluded. In consideration of such characteristics of the exosomes, cell therapy using exosomes is expected to be a new paradigm for overcoming the limitations of existing stem cell therapy.

In this regard, in Korean Unexamined Patent Application No. 2012-0133709, a skin regeneration effect of exosomes obtained from skin cells has been disclosed, but it has never been known that exosomes derived from thrombin-treated stem cells are more highly effective in treatment of skin wounds, compared with the conventional method.

SUMMARY

Technical Problem

Therefore, the inventors had intensively studied to overcome the limitations of stem cell therapeutic agents and improve therapeutic efficacy in terms of skin wounds, and as a result, they confirmed that exosomes derived from stem cells, especially from stem cells treated with thrombin, remarkably increase angiogenesis and a skin wound healing effect, thereby completing the present disclosure.

Accordingly, the present disclosure is directed to providing a pharmaceutical composition for preventing or treating skin wounds, which includes exosomes derived from thrombin-treated stem cells.

However, technical problems to be solved in the present disclosure are not limited to the above-described problems, and other problems which are not described herein will be fully understood by those of ordinary skill in the art from the following descriptions.

Technical Solution

The present disclosure provides a pharmaceutical composition for preventing or treating skin wounds, which includes exosomes derived from thrombin-treated stem cells as an active ingredient.

In one exemplary embodiment of the present disclosure, the stem cells are stem cells selected from the group consisting of mesenchymal stem cells, human tissue-derived mesenchymal stromal cells, human tissue-derived mesenchymal stem cells and multipotent stem cells.

In another exemplary embodiment of the present disclosure, the mesenchymal stem cells are derived from umbilical cord, umbilical cord blood, bone marrow, fat, muscle, nerve, skin, amniotic membrane or placenta.

In still another exemplary embodiment of the present disclosure, the treatment of skin wounds is carried out by angiogenesis due to promotion of vascular endothelial cell growth.

In yet another exemplary embodiment of the present disclosure, the skin wounds result from the loss of epidermis, dermis or subcutaneous tissue.

In yet another exemplary embodiment of the present disclosure, the pharmaceutical composition is administered via an oral or non-oral route.

In yet another exemplary embodiment of the present disclosure, the pharmaceutical composition further includes a supplementary ingredient selected from the group consisting of a culture medium, a cytokine, a growth factor and a gene.

In yet another exemplary embodiment of the present disclosure, the exosomes are increased in the expression of a growth factor, an immunoregulatory factor, an antioxidation factor or an angiogenesis factor.

In yet another exemplary embodiment of the present disclosure, the growth factor is a brain-derived neurotropic factor (BDNF), a fibroblast growth factor (FGF), a hepatocyte growth factor (HGF), a nerve growth factor (NGF), or a vascular endothelial growth factor (VEGF).

The present disclosure also provides a pharmaceutical formulation for preventing or treating skin wounds, which includes the composition of the present disclosure.

In one exemplary embodiment of the present disclosure, the formulation is an injection type, a suppository type, a spray type, a liquid type, or a patch type.

In another exemplary embodiment of the present disclosure, the preparation further includes a pharmaceutically acceptable carrier.

The present disclosure also provides a quasi-drug for improving skin wounds, which includes exosomes derived from thrombin-treated stem cells as an active ingredient.

In one exemplary embodiment of the present disclosure, the improvement of skin wounds results from angiogenesis.

In another exemplary embodiment of the present disclosure, the exosomes are increased in the expression of a growth factor, an immunoregulatory factor, an antioxidation factor or an angiogenesis factor.

In still another exemplary embodiment of the present disclosure, the quasi-drugis in the form of a skin external preparation selected from the group consisting of a liquid, an ointment, a cream, a spray, a patch, a gel and an aerosol.

The present disclosure also provides a method of preparing the pharmaceutical composition, which includes: (a) culturing stem cells and treating the stem cells with thrombin; (b) isolating exosomes from the culture solution of Step (a); and (c) preparing a composition containing the exosomes isolated in Step (b) as an active ingredient.

In one exemplary embodiment of the present disclosure, the thrombin of Step (a) is contained at a concentration of 1 to 1000 unit/mL in the medium.

In another exemplary embodiment of the present disclosure, the exosomes of Step (c) are subjected to centrifugation.

In still another exemplary embodiment of the present disclosure, the centrifugation is performed at 5,000 to 500,000 g for 10 minutes to 5 hours.

The present disclosure also provides a method of treating skin wounds, which includes administering exosomes derived from thrombin-treated stem cells to a subject.

The present disclosure also provides a use of exosomes derived from thrombin-treated stem cells to prepare a preparation for preventing or treating skin wounds.

Advantageous Effects

Since an exosome-based therapeutic agent of the present disclosure is a cell-free preparation and does not contain DNA, there is less risk of carcinogenesis, and because there are no cell surface antigens, there is no problem of transplantation rejection.

In addition, since an exosome-based therapeutic agent is much smaller than cells, there is no risk of obstruction of microvascular vessels during systemic administration, and as it is an isolated material, rather than cells, it can be developed as an off-the-shelf medication, resulting in a reduction in production costs.

Moreover, compared with non-treated stem cells, since exosomes derived from thrombin-treated stem cells exhibit an excellent skin wound-treating effect even at a small amount, a required amount of stem cells for producing a therapeutically effective amount of exosomes is remarkably reduced, thereby significantly reducing the production costs of a therapeutic agent.

Therefore, according to the present disclosure, problems resulting from the conventional stem cell therapeutic agent can be resolved, and as therapeutic efficacy can be significantly improved, the exosome-based therapeutic agent can be effectively used in treatment of skin wounds.

DETAILED DESCRIPTION

Figure 1:
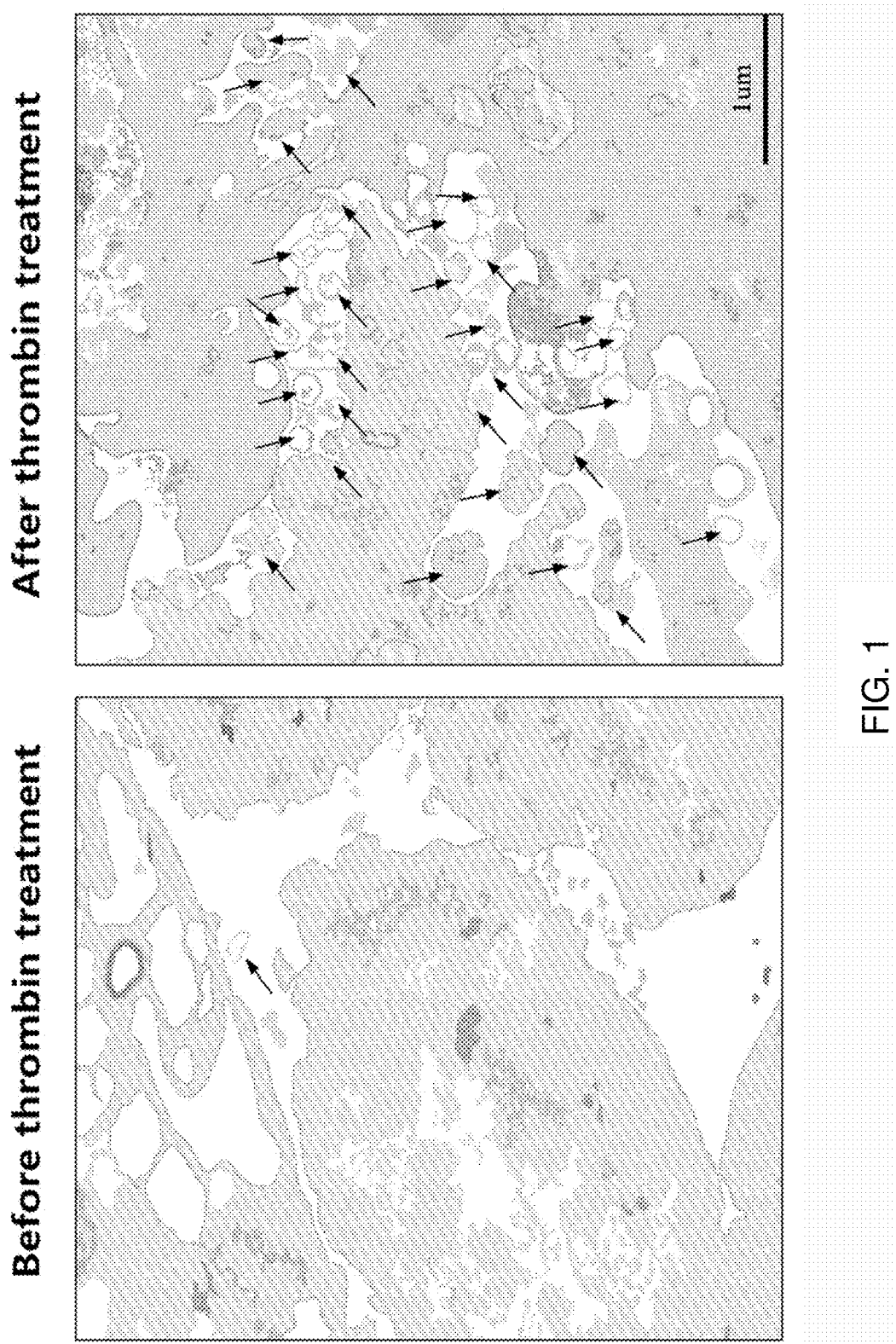
FIG. 1 shows a process of activating the secretion of exosomes in treatment of stem cells with thrombin, confirmed by TEM image analysis.

The present disclosure provides a pharmaceutical composition for preventing or treating skin wounds, which includes exosomes derived from thrombin-treated stem cells as an active ingredient.

The term "stem cells" used herein refers to undifferentiated cells, which have a self-renewal ability and an ability to be differentiated into two or more different types of cells. The stem cells of the present disclosure may be autologous or allogeneic stem cells, which may be derived from arbitrary types of animals including a human and a non-human mammal, and may be derived from adult stem cells or embryonic stem cells, but the present disclosure is not limited thereto.

The stem cells of the present disclosure may include embryonic stem cells or adult stem cells, and preferably adult stem cells. The adult stem cells may be mesenchymal stem cells, human tissue-derived mesenchymal stromal cells, human tissue-derived mesenchymal stem cells or multipotent stem cells, and preferably mesenchymal stem cells, but the present disclosure is not limited thereto. The mesenchymal stem cells may be mesenchymal stem cells derived from umbilical cord, umbilical cord blood, bone marrow, fat, muscle, nerve, skin, amniotic membrane or placenta, but the present disclosure is riot limited thereto.

The term "umbilical cord blood" used herein refers to blood taken from the umbilical vein connecting the placenta and fetus. The umbilical cord blood is a naturally-occurring byproduct in birth, even more easily taken than general mesenchymal tissue derived from the bone marrow requiring several operations, and compared with bone marrow transplantation, since the infrastructure relevant to the umbilical cord blood has been already constructed due to activation of the umbilical cord blood storage industry, it is easy to find a donor. In addition, since the umbilical cord blood-derived cells are cells which do not express a tissue-compatible antigen. HLA-DR (class II), which is the most important cause of rejection in tissue or organ transplantation, the umbilical cord blood-derived cells may not induce or minimize an immune response such as rejection, which has been problematic in an conventional transplantation operation, thus, xenogeneic umbilical cord blood as well as autologous umbilical cord blood can be used.

The term "exosome" refers to small vesicles (approximately 30 to 100 in diameter) having a membrane structure, which are secreted from various cells, and refers to vesicles which are released into an extracellular environment due to fusion between MVBs and a plasma membrane. The exosomes are naturally or artificially secreted.

The term "skin wound" used herein refers to the loss of epidermis, dermis or subcutaneous tissue.

The term "prevention or treatment of skin wounds" used herein includes relief, alleviation and symptom improvement of skin wounds, and refers to a reduction in the possibility of generating skin wounds. In the present disclosure, by treating vascular endothelial cells (e.g., HUVEC) with the thrombin-treated stem cells of the present disclosure, it was confirmed that blood vessels are newly generated by promoting the growth of the vascular endothelial cells.

Angiogenesis is a phenomenon in which existing vascular endothelial cells form new capillary vessels by degrading, migrating, dividing and differentiating the ECM, and is necessarily exhibited in the physiological process of wound healing. The wound healing effect can be verified by confirming the angiogenesis effect. That is, angiogenesis should be involved in an essential wound healing process to regenerate injured skin tissue. In the early stage of a wound, an inflammation response is caused by necrosis of cells and destruction of blood vessels, and after the inflammation response, along with a phenomenon of detachment of blood components from a blood vessel, activation of platelets and blood coagulation, a series of processes for forming biological mediators such as kallikrein, thrombin and plasmin are carried out.

In the present disclosure, compared with non-treated stem cells, the "thrombin-treated stem cells" may have reinforced stem cell function/efficacy due to a main action mechanism of stem cells, which is an increase in paracrine property, without a change in cell stability indicated by cell viability, an oxidative function, etc. Further, thrombin treatment can reinforce the therapeutic efficacy of exosomes derived from stem cells, and also increase a secretion amount of the exosomes, At this time, as a paracrine function, a growth factor, an immunoregulatory factor, an antioxidation factor or a regenerative factor may be increased, wherein the growth factor refers to a proteinaceous, physiologically active material which promotes cell division, growth or differentiation, and includes a brain-derived neurotropic factor (BDNF), a fibroblast growth factor (FGF), a hepatocyte growth factor (HGF), a nerve growth factor (NGF), a vascular endothelial growth factor (VEGF), and interleukin-6 (IL-6). Particularly, the vascular endothelial cell growth factor (VEGF) is a representative protein which regulates vessel formation. VEGF binds to VEGF receptor 1, 2 or 3 (VEGFR1, VEGFR2 or VEGFR3), present in vascular endothelial cells and results in tyrosine phosphorylation of a VEGF receptor (VEGFR), thereby the activation of vascular endothelial cells, and such activation ultimately has a critical effect on angiogenesis.

The pharmaceutical composition of the present disclosure may be administered to a subject via various routes without particular limitation, and for example, may be administered via an oral or non-oral route.

The pharmaceutical composition of the present disclosure may further contain one or more known supplementary ingredients having a therapeutic effect on skin wounds, in addition to stem cell-derived exosomes. For example, the pharmaceutical composition of the present disclosure may further include a supplementary ingredient selected from the group consisting of a gene effective in skin wound treatment (e.g., an anti-inflammatory cytokine gene, or siRNA or an antisense primer for an inflammatory cytokine) or an expression vector including the same, a cytokine providing an autocrine or paracrine effect (e.g., interleukin-10), a growth factor keratinocyte growth factor) and a combination thereof.

A preferable dose of the pharmaceutical composition of the present disclosure may depend on a subject's condition and body weight, the severity of a disease, a drug type, an administration route and administration duration, and may be suitably selected by those of ordinary skill in the art. The administration of the composition may be administered once or in divided doses, per day, but the present disclosure is not limited thereto.

The pharmaceutical composition of the present disclosure may be used individually, or in combination with methods using surgery, radiation therapy, hormone therapy, chemotherapy and a biological action regulator to treat skin wounds.

The composition of the present disclosure may further include a suitable carrier, which is conventionally used in preparation of a pharmaceutical composition. For example, an injection may further include a preservative, an analgesic, a solubilizer or a stabilizer, and a preparation for local administration may further include a base, an excipient, a lubricant or a preservative.

The composition of the present disclosure may be administered by being formulated into a unit dosage form suitable for administration into a body according to a method conventionally used in the pharmaceutical field. A suitable formulation for this purpose is preferably a preparation for non-oral administration, for example, an injection such as an injectable ampoule, an injection such as an injection bag, and a sprayer such as an aerosol preparation. The injectable ampoule may be prepared by being mixed with an injection solution immediately before use, and the injection solution may be physiological saline, glucose or Ringer's solution. In addition, the injection bag may be formed of polyvinyl chloride or polyethylene. In the present disclosure, administration refers to providing the composition of the present disclosure to a subject by any suitable method.

A preferable dose of the pharmaceutical composition of the present disclosure may depend on a subject's condition and body weight, the severity of a disease, a drug type, an administration route and administration duration, and may be suitably selected by those of ordinary skill in the art. The administration of the composition may be administered once or in divided doses, per day, but the present disclosure is not limited thereto.

In addition, the present disclosure provides a quasi-drug for improving skin wounds, which includes exosomes derived from thrombin-treated stem cells as an active ingredient.

In the present disclosure, the quasi-drug may be a dermal preparation for external use selected from the group consisting of a liquid, an ointment, a cream, a spray, a patch, a gel and an aerosol, and specifically, may be used as a composition for a sanitizer, a shower foam, a mouthwash, a wet tissue, a detergent, soap, hand wash, a humidifier refill, a mask, an ointment or a filter refill.

The present disclosure also provides a method of preparing the pharmaceutical composition, which includes: (a) culturing stem cells and treating the stem cells with thrombin; (b) isolating exosomes from the culture solution of Step (a); and (c) preparing a composition containing the exosomes isolated in Step (b) as an active ingredient.

In the present disclosure, a treatment concentration of thrombin is a concentration suitable for reinforcing the efficacy of stem cells/exosomes, and thrombin is preferably contained at 1 to 1000 unit/mL in a medium, but the present disclosure is not particularly limited thereto.

In the present disclosure, there is no limitation to a method of isolating exosomes, and exosomes may be isolated from a culture solution by a method such as centrifugation, ultracentrifugation, filtration through a filter, gel filtration chromatography, pre-flow electrophoresis, capillary electrophoresis, isolation using a polymer, and a combination thereof, and preferably, centrifugation/ultracentrifugation. Here, the centrifugation/ultracentrifugation is preferably performed at 4° C. and 3,000 to 100,000 g for 10 minutes to 5 hours.

The medium used in cell culture in the present disclosure refers to a mixture for in vitro cell growth and proliferation of stem cells, which includes essential factors for cell growth and proliferation, such as sugar, an amino acid, various nutrients, serum, a growth factor, a mineral, etc. The medium used in the present disclosure may be any one of commercially-produced media including Dulbecco's Modified Eagle's Medium (DMEM), Minimal Essential Medium (MEM), Basal Medium Eagle (BME), RPMI1640, Dulbecco's Modified Eagle's Medium: Nutrient Mixture F-10 (DMEM/F-10), Dulbecco's Modified Eagle's Medium: Nutrient Mixture F-12 (DMEM/F-12), a-Minimal essential Medium (a-MEM), Glasgow's Minimal Essential Medium (G-MEM), Isocove's Modified Dulbecco's Medium (IMDM) and Knockout DMEM, or an artificially synthesized medium, but the present disclosure is not limited thereto.

The present disclosure also provides a method of treating skin wounds, which includes administering exosomes derived from thrombin-treated stem cells to a subject.

The term "subject" used herein refers to a subject in need of treatment, and more specifically, a mammal such as a human, or a non-human primate, a mouse, a rat, a dog, a cat, a horse and a cow.

Hereinafter, to help in understanding the present disclosure, exemplary examples will be suggested. However, the following examples are merely provided to more easily understand the present disclosure, and not to limit the present disclosure.

EXAMPLES

Example 1

Induction of Secretion of Exosomes and Efficacy Improvement by Treating Stem Cells With Thrombin 1-1. Induction of Exosome Secretion Due to Thrombin Human umbilical cord blood-derived mesenchymal stem cells ($3\times10^5$ cells) were seeded in a 100 mm culture dish (Orange Scientific cat# 4450200) and cultured for one week. After the cells were saturated and proliferated in the culture dish, the medium was replaced with a serum-free culture medium (MEM alpha media) in which 50 unit/mL thrombin (REYON Pharmaceutical. Co., Ltd.) was diluted, and then cultured again for 6 hours.

Here, to confirm whether the secretion of exosomes is activated in mesenchymal stem cells by treatment of thrombin, a process of the exosome secretion was confirmed through transmission electronic microscopy (TEM) images. As a result, as shown in FIG. 1, it can be seen that stimulation by thrombin results in exosome secretion.

Afterward, the culture solution was distributed into centrifuge tubes to perform centrifugation at 4° C. and 6,000 rpm for 30 minutes, and a supernatant was transferred to new tubes to remove cell debris. Again, the supernatant was subjected to ultracentrifugation at 4° C. and 100,000 rpm for 2 to 4 hours, and then a supernatant was further removed, thereby obtaining exosomes (final concentration: 15 μg/mL).

Figure 2:
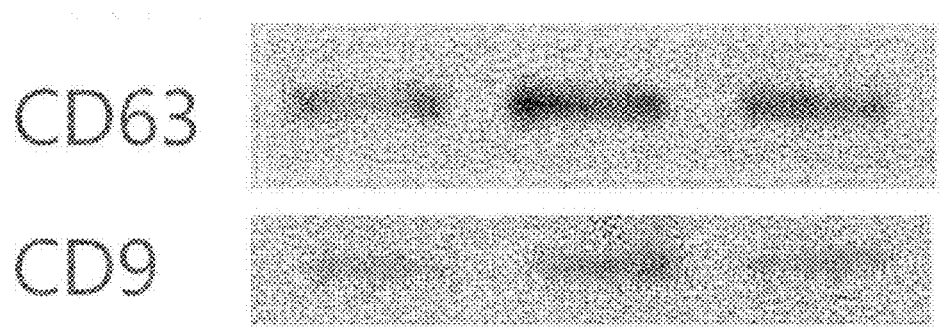
FIG. 2 shows a western blotting result confirming that exosomes derived from thrombin-treated stem cells normally express CD63 and CD9, which are exosome markers.

Here, to confirm whether the obtained product was a suitable exosome, the expression of CD63 and CD9 (System Biosciences, Mountain View, Calif., USA), which are known exosome markers, was verified by western blotting. As a result, as shown in FIG. 2, as the exosomes obtained from the thrombin-treated stem cells normally expressed CD63 and CD9, indicating that they were the exosomes of the present disclosure.

1-2. Improvement in Exosome Efficacy Due to Thrombin

It was confirmed whether the exosomes obtained in Example 1-1 were increased in the expression of a growth factor or an anti-inflammatory cytokine such as IL-6 due to thrombin treatment.

Specifically, after the exosome membrane was dissolved in a lysis buffer, proteins in exosomes were isolated to measure BDNF, FGF, HGF, NGF, VEGF and IL-6 levels in the exosomes using a Procarta immunoassay kit (Affymetrix, USA).

Figure 3:
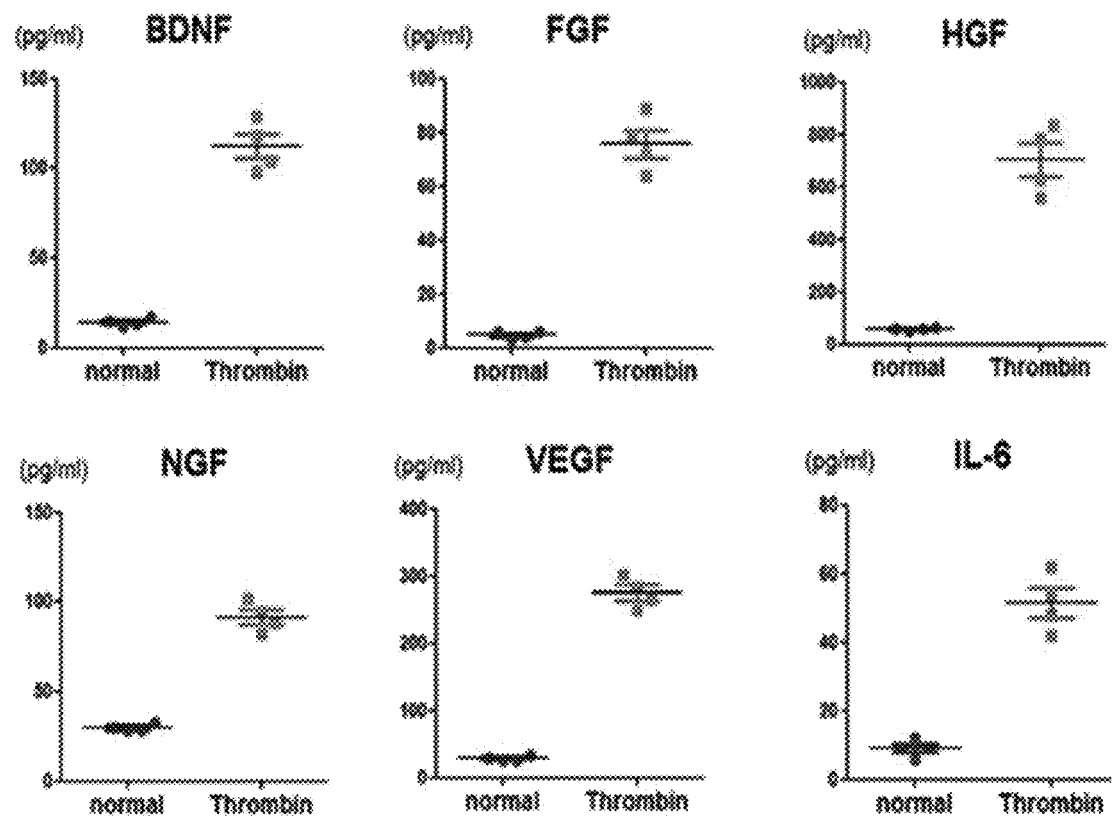
FIG. 3 shows an immunoassay result showing that the expression of growth factors (BDNF, FGF, HGF, NGF and VEGF) and an anti-inflammatory cytokine (IL-6) in exosomes is increased by thrombin treatment.

As a result, as shown in FIG. 3, it was confirmed that the expression of a brain-derived neurotropic factor (BDNF), a fibroblast growth factor (FGF), a hepatocyte growth factor (HGF), a nerve growth factor (NGF), a vascular endothelial growth factor (VEGF) and interleukin-6 (IL-6) in exosomes was increased due to thrombin treatment, compared with exosomes obtained from non-thrombin treated-stem cells (control, normal).

This result indicates that cell regeneration, blood vessel regeneration and anti-inflammatory efficacy of the stem cell-derived exosomes are increased due to thrombin treatment.

Example 2

In Vitro Angiogenesis Effect: Tube Formation Assay

2-1. Effect According to Exosome Concentration

To confirm whether the "exosomes derived from thrombin-treated stem cells" used herein affect tube formation (angiogenesis) by inducing differentiation of vascular endothelial cells, a tube forming assay was performed using growth factor-reduced Matrigel (10 mg/mL).

Specifically, human umbilical vein endothelial cells (HUVECs) were cultured in Low Serum Growth Supplement (LSGS)-containing Medium 200PRF for 12 hours, treated with trypsin to collect the cells, and resuspended in a 5% fetus bovine serum-containing M199 medium. Growth factor-reduced Matrigel was added into each well of a 24-well plate at 250 μL, and polymerized at 37° C. in a $CO_2$ incubator. The HUVEC cells were added to each well containing the polymerized Matrigel at $4 \times 10^4$ cells/well, and the thrombin-treated stem cell-derived exosomes used in Example 1 were added at 2.5 μg/mL, 5 μg/mL or 10 μg/mL. The HUVECs were cultured for 24 hours at 37° C. in a $CO_2$ incubator, the cell culture was photographed (×40), and a length of the formed rube was measured using ImageJ (National Institute of Health), a public domain program.

Figure 4A:
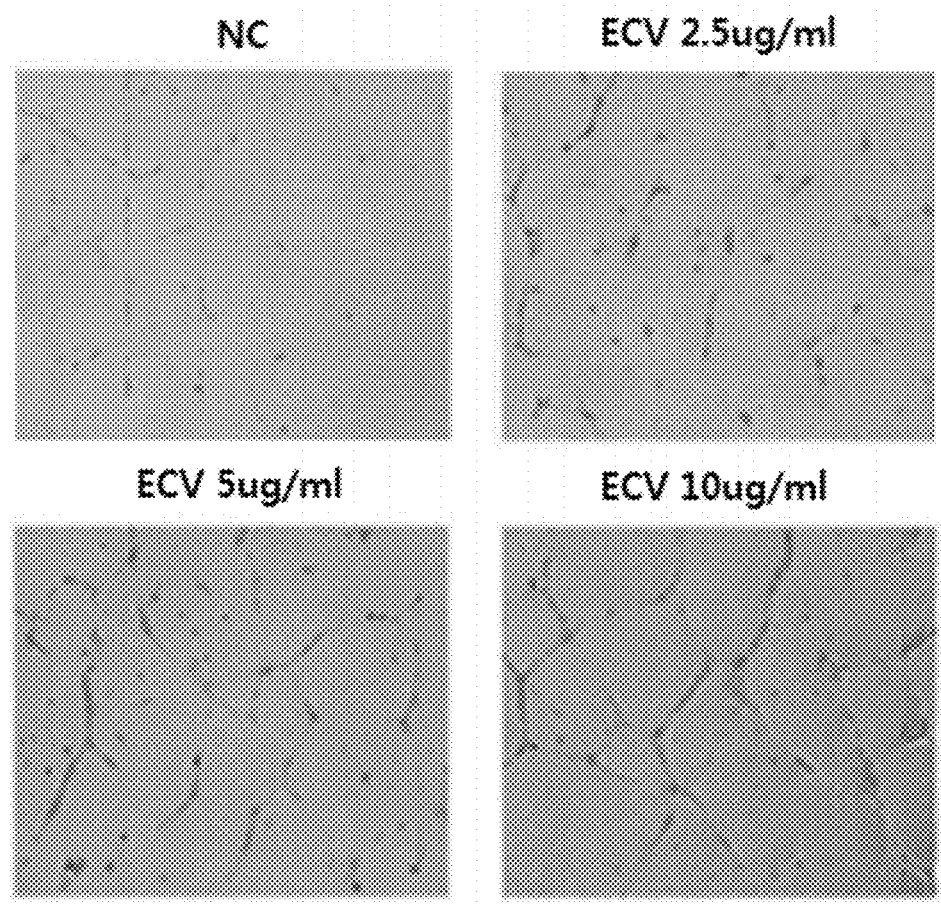
FIG. 4A is a tube formation assay result showing that exosomes derived from thrombin-treated stem cells dose-dependently exhibit an angiogenesis effect.
Figure 4B:
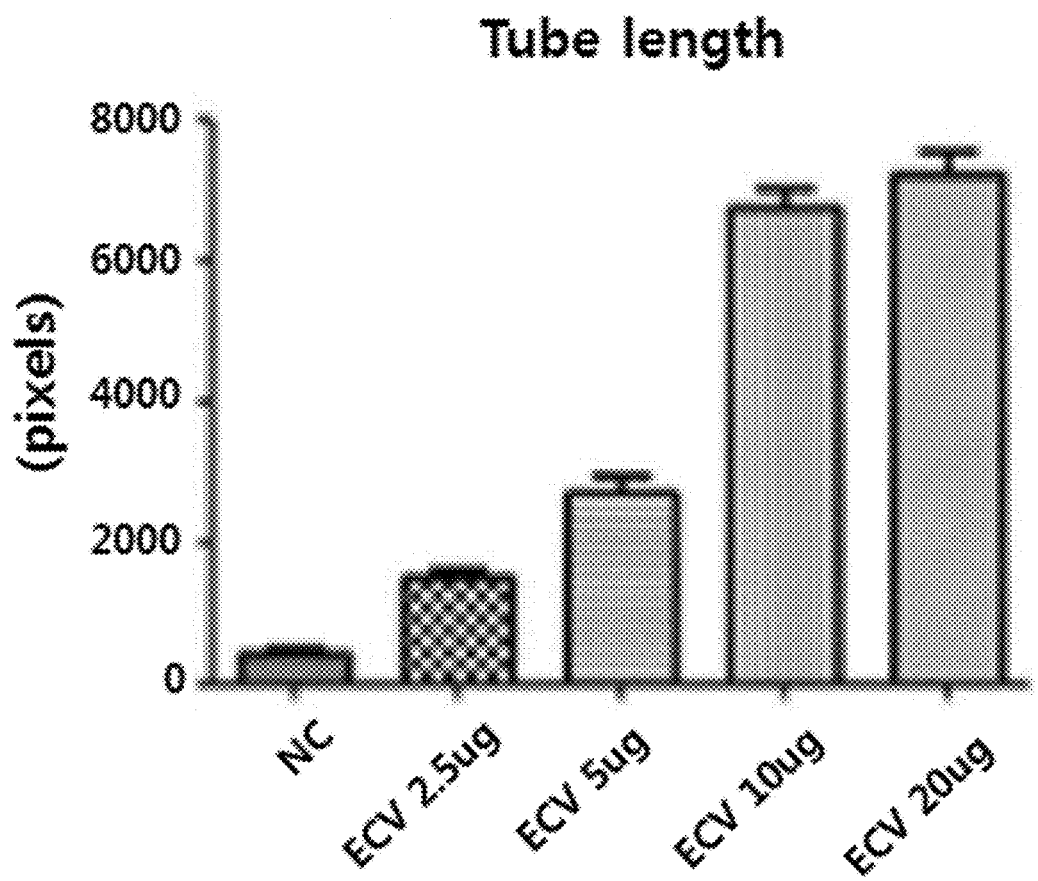
FIG. 4B is a graph quantifying the tube formation assay result.

As a result, as shown in FIGS. 4A and 4B, the thrombin-treated stem cell-derived exosomes of the present disclosure dose-dependently induced the differentiation of vascular endothelial cells, compared with a control (non-treated NCs), thereby improving tube formation.

2-2. Evaluation Per Exosome-Derived Cell

An experiment was carried out in the same manner as in Example 2-1, except that HUVEC cells were treated with non-thrombin-treated stem cell-derived exosomes (MSC ECV), thrombin-treated stem cell-derived exosomes (MSC throm ECV), non-thrombin-treated fibroblast-derived exosomes (fibroblast ECV), or thrombin-treated fibroblast-derived exosomes (fibroblast throm ECV) at 10 μg/mL.

Figure 5A:
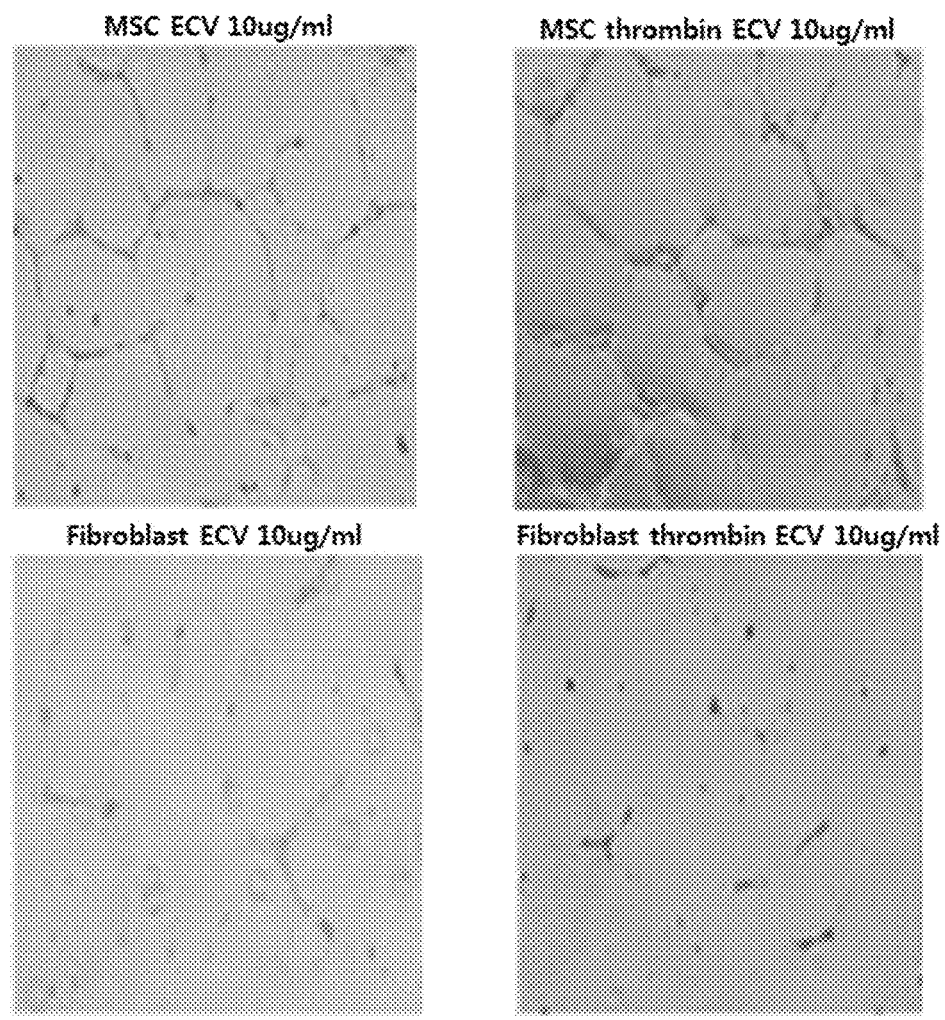
FIG. 5A shows a tube formation assay result showing that there is a difference in angiogenesis effect depending on the type of cells from which exosomes are derived
Figure 5B:
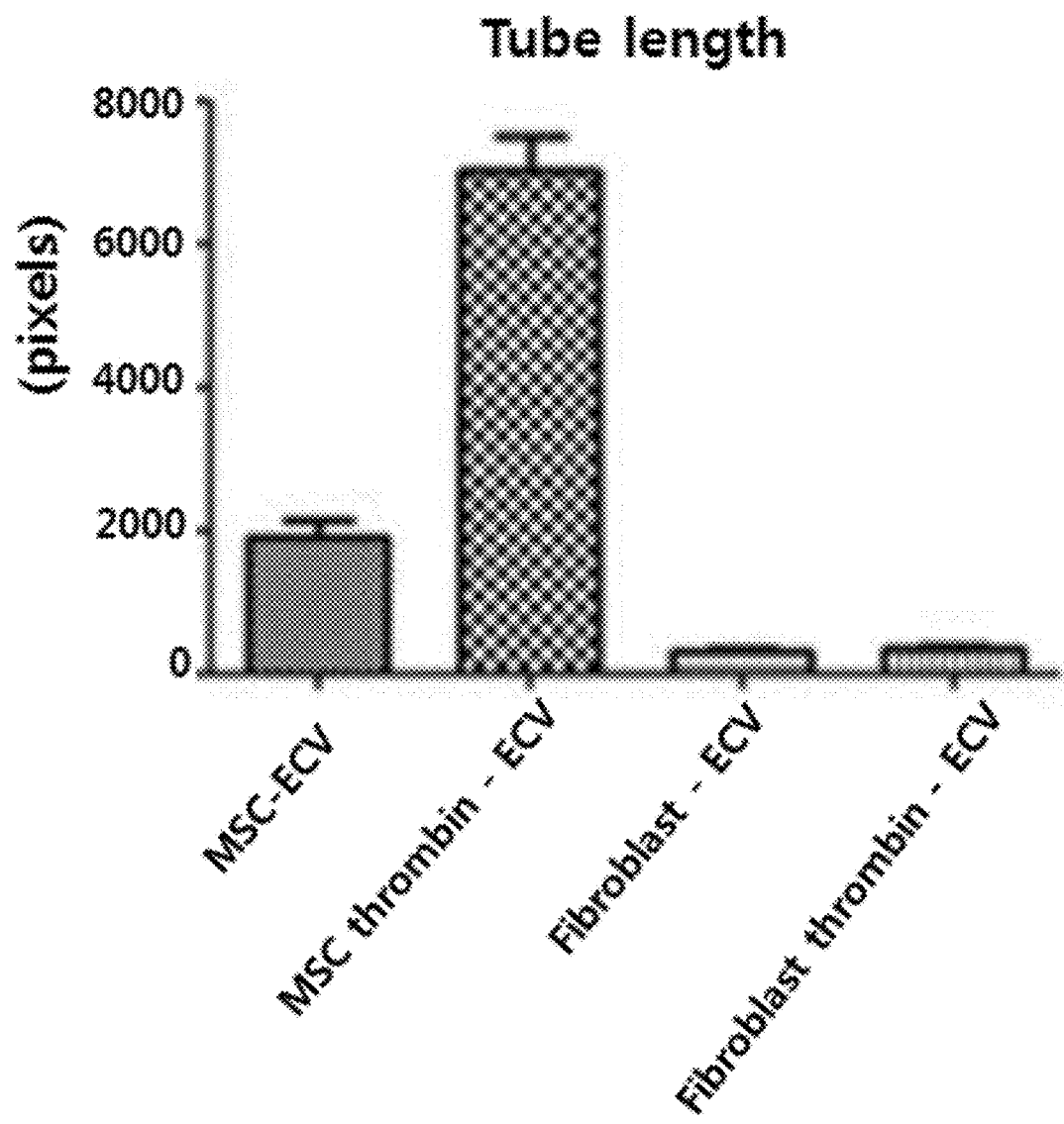
FIG. 5B shows a graph quantifying the tube formation assay result.

As a result, as shown in FIGS. 5A and 5B, the thrombin-treated stem cell-derived exosomes (MSC throm ECV) of the present disclosure exhibited a significantly improved angiogenesis ability, compared with the non-thrombin-treated, stem cell-derived exosomes (MSC ECV). In addition, the fibroblast-derived exosomes did not exhibit an angiogenesis ability regardless of thrombin treatment, suggesting that therapeutic efficacy (angiogenesis ability) is specifically determined according to the type/ability of cells from which exosomes are derived.

Example 3

In Vivo Skin Wound Treating Effect

All animal experiments were approved by the Research Animal Laboratory Committee of Samsung Biomedical Research Institute (Korea), and the guidelines of this organization were followed.

First, after the skin was punched with a 0.8 mm biopsy punch at a dorsal region of an adult rat to manufacture a skin wound animal model, 20 μg of fibroblast-derived exosomes (fibroblast exosome), non-thrombin-treated, stem cell-derived exosomes (naive MSC exosome), or thrombin-treated stem cell-derived exosomes (thrombin MSC exosome) were mixed with saline to prepare a total 10 μL preparation, and then the preparation was applied to a wound surface.

Figure 6A:
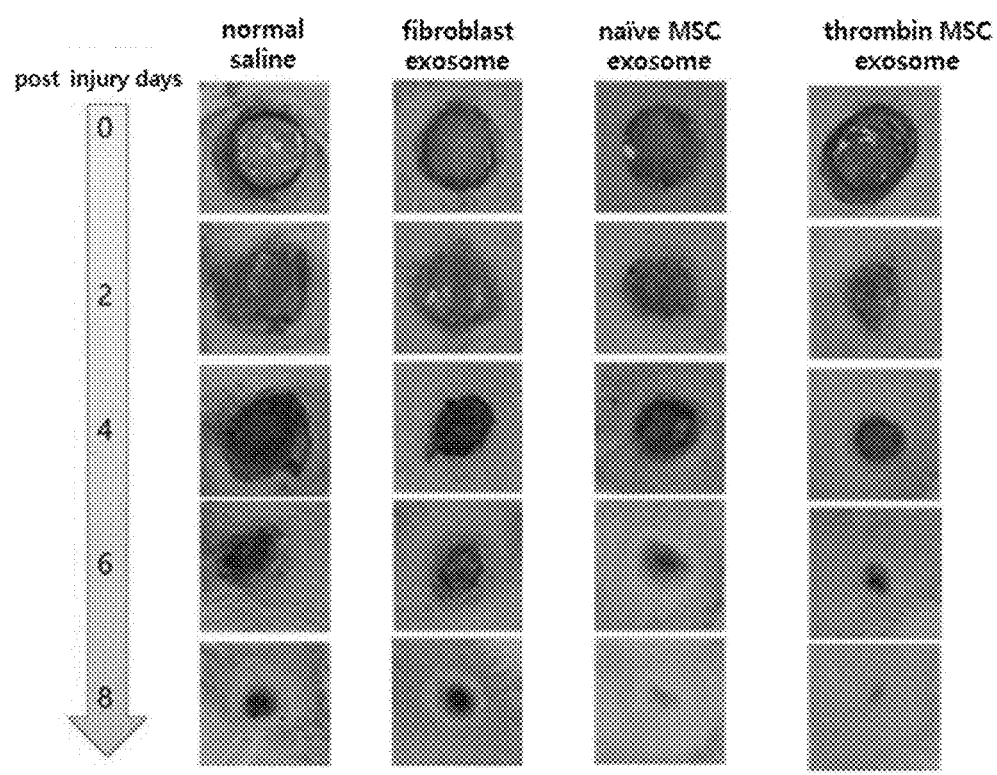
FIG. 6A shows a result showing a skin wound healing effect on exosomes derived from thrombin-treated stem cells in in vivo skin wound animal models.
Figure 6B:
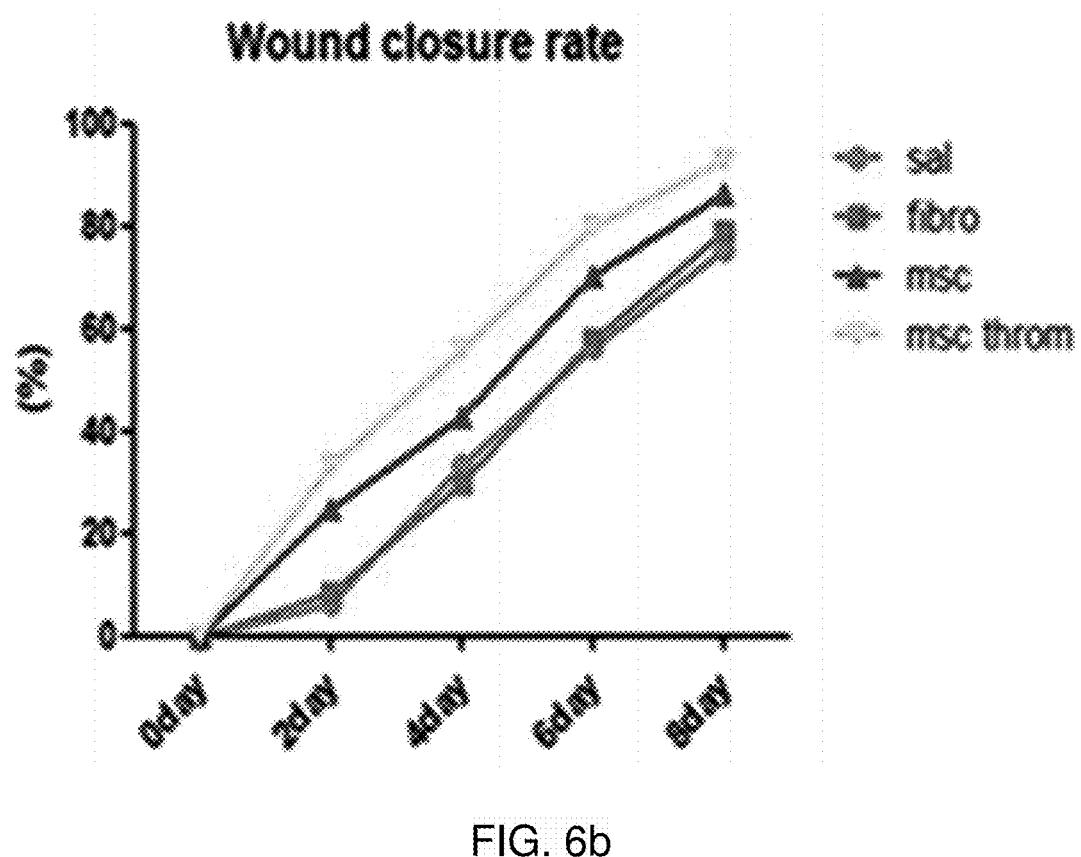
FIG. 6B shows a graph quantifying the tube formation assay result.

As a result, as shown in FIGS. 6A and 6B, the thrombin-treated stem cell-derived exosomes (thrombin MSC exosome) of the present disclosure exhibited a significantly improved wound treating effect, compared with non-thrombin-treated, stem cell-derived exosomes (naive MSC exosome). In addition, it can be confirmed that the fibroblast-derived exosomes did not exhibit a wound treating effect, similar to a control (saline).

In addition, after an injury was induced by punch biopsy after the dorsal region of SD-rat was shaved, fibroblast-derived exosomes (fibroblast exosome), non-thrombin-treated, stem cell-derived exosomes (naive MSC exosome), thrombin-treated stem cell-derived exosomes (thrombin MSC exosome) or hypoxia-pretreated stem cell-derived exosomes (hypoxia MSC exosome) were applied, and then skin recovery was checked.

Figure 7:
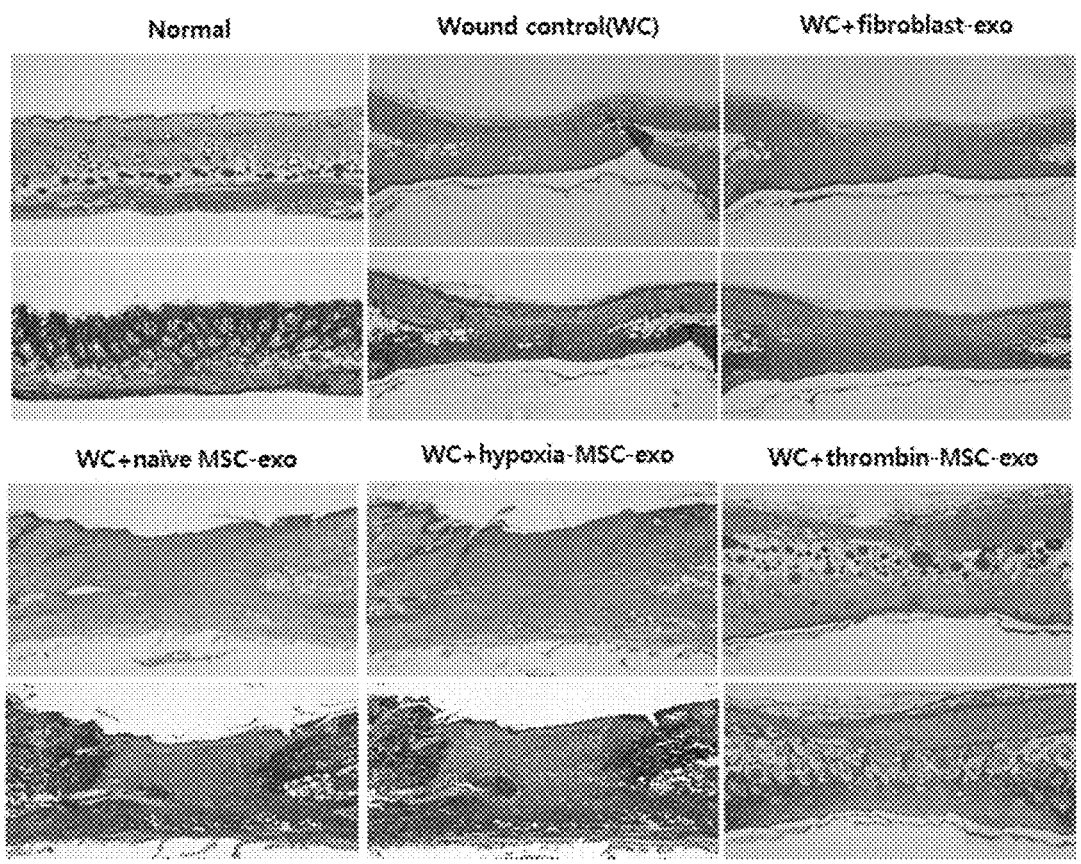
FIG. 7 shows skin wound healing effects of fibroblast-derived exosomes (fibroblast exosome), non-thrombin-treated stem cell-derived exosomes (naive MSC exosome), thrombin-treated stem cell-derived exosomes (thrombin MSC exosome) and hypoxia-pretreated stem cell-derived exosomes (hypoxia MSC exosome) in in vivo skin wound animal models.

As a result, as shown in FIG. 7, it was shown that, compared with a normal group (Normal), in a wound control (WC), the injured skin caused by punch biopsy cannot recover to normal skin tissue, and the same result was shown when the fibroblast-derived exosomes were administered. On the other hand, the non-thrombin-treated, stem cell-derived exosomes (naive MSC exosome) and the hypoxia-pretreated stem cell-derived exosomes (hypoxia MSC exosome) showed a tendency to be slightly improved, and the thrombin-treated stem cell-derived exosomes (thrombin MSC exosome) showed a skin recovery state close to normal tissue, and thus exhibited a significantly improved wound treating effect.

These results showed that therapeutic efficacy is determined specifically according to the type/ability of cells from which exosomes are derived.

It should be understood by those of ordinary skill in the art that the above description of the present disclosure is exemplary, and the exemplary embodiments disclosed herein can be easily modified into other specific forms without departing from the technical spirit or essential features of the present disclosure. Therefore, the exemplary embodiments described above should be interpreted as illustrative and not limited in any aspect.

INDUSTRIAL APPLICABILITY

According to a therapeutic agent based on thrombin-treated stem cell-derived exosomes according to the present disclosure, a problem of the conventional stem cell therapeutic agent, such as transplantation rejection or production costs, can be solved and therapeutic efficacy can be significantly improved, and therefore the therapeutic agent can be effectively used in treatment of skin wounds.

What is claimed is:

1. A method of treating skin wound, comprising:
   administering to a subject in need thereof an effective amount of exosomes derived from thrombin-treated stem cells.

2. A method according to claim 1, wherein the stem cells are selected from the group consisting of mesenchymal stem cells, human tissue-derived mesenchymal stromal cells, human tissue-derived mesenchymal stem cells and multipotent stem cells.

3. A method according to claim 2, wherein the mesenchymal stem cells are derived from umbilical cord, umbilical cord blood, bone marrow, fat, muscle, nerve, skin, amniotic membrane or placenta.

4. A method according to claim 1, wherein the treatment of skin wounds is caused by angiogenesis due to the promotion of the growth of vascular endothelial cells.

5. A method according to claim 1, further comprising:
   administering to a subject in need thereof an effective amount of a supplementary ingredient selected from group consisting of a culture medium, a cytokine, a growth factor and a gene.

6. A method according to claim 1, wherein the exosomes are increased in the expression of a growth factor, an immunoregulatory factor, an antioxidation factor or an angiogenesis factor.

7. A method according to claim 6, wherein the growth factor is a brain-derived neurotropic factor (BDNF), a fibroblast growth factor (FGF), a hepatocyte growth factor (HGF), a nerve growth factor (NGF), or a vascular endothelial growth factor (VEGF).

\* \* \* \* \*